(12) United States Patent
Shubinsky et al.

(10) Patent No.: US 8,701,465 B2
(45) Date of Patent: Apr. 22, 2014

(54) PHOTOACOUSTIC SENSOR DIFFUSION MEMBRANE ATTACHMENT STRUCTURE

(75) Inventors: Gary P. Shubinsky, Buffalo Grove, IL (US); Thomas M. Rezachek, Cottage Grove, MN (US); Michael J. Koch, Roselle, IL (US); Takashi Yamaguchi, Lake Forest, IL (US)

(73) Assignee: Honeywell International Inc., Morristown, NJ (US)

( * ) Notice: Subject to any disclaimer, the term of this patent is extended or adjusted under 35 U.S.C. 154(b) by 380 days.

(21) Appl. No.: 13/096,883

(22) Filed: Apr. 28, 2011

(65) Prior Publication Data

US 2012/0272716 A1 Nov. 1, 2012

(51) Int. Cl.
*G01N 21/17* (2006.01)
(52) U.S. Cl.
USPC .......................................... 73/24.02
(58) Field of Classification Search
USPC ................... 73/24.02; 356/432, 450; 250/343
See application file for complete search history.

(56) References Cited

U.S. PATENT DOCUMENTS

| | | | | |
|---|---|---|---|---|
| 2,449,166 A * | 9/1948 | Hershberger | ................. | 359/285 |
| 2,907,121 A * | 10/1959 | Yelinek et al. | ................. | 434/367 |
| 3,121,169 A * | 2/1964 | Benton | ........................ | 398/201 |
| 5,053,754 A * | 10/1991 | Wong | ............................ | 340/632 |
| 5,616,826 A * | 4/1997 | Pellaux et al. | ............... | 73/24.02 |
| 6,006,585 A * | 12/1999 | Forster | ........................ | 73/24.01 |
| 6,012,325 A * | 1/2000 | Ma | ............................... | 73/24.02 |
| 6,067,840 A * | 5/2000 | Chelvayohan et al. | ........ | 73/23.2 |
| 6,672,135 B2 * | 1/2004 | Adiletta | ..................... | 73/28.04 |
| 7,091,869 B2 * | 8/2006 | Forster et al. | ................. | 340/628 |
| 7,170,607 B2 * | 1/2007 | Yoon et al. | .................... | 356/437 |
| 7,304,742 B1 * | 12/2007 | Gurton | ......................... | 356/432 |
| 7,656,532 B2 * | 2/2010 | Cole | ............................. | 356/432 |
| 2002/0092340 A1 * | 7/2002 | Prater et al. | ................. | 73/24.02 |
| 2005/0121614 A1 | 6/2005 | Stuttard | ....................... | 250/343 |
| 2008/0242979 A1 * | 10/2008 | Fisher et al. | ................. | 600/427 |
| 2008/0257016 A1 * | 10/2008 | Fujii et al. | .................... | 73/31.05 |
| 2009/0266144 A1 * | 10/2009 | Rezachek | .................... | 73/24.02 |
| 2009/0320561 A1 * | 12/2009 | Fritz et al. | .................... | 73/24.02 |
| 2010/0018288 A1 * | 1/2010 | Yamanaka et al. | ........... | 73/24.02 |
| 2010/0027012 A1 | 2/2010 | Fritz et al. | .................... | 356/432 |
| 2010/0045998 A1 | 2/2010 | Fritz et al. | .................... | 356/450 |
| 2010/0147051 A1 | 6/2010 | Tobias | ......................... | 73/24.02 |
| 2010/0297856 A1 * | 11/2010 | Moffatt et al. | ................ | 438/795 |
| 2013/0008229 A1 * | 1/2013 | Avramescu et al. | ......... | 73/24.02 |
| 2013/0008230 A1 * | 1/2013 | Avramescu et al. | ......... | 73/24.02 |

* cited by examiner

*Primary Examiner* — John Fitzgerald
(74) *Attorney, Agent, or Firm* — Husch Blackwell LLP

(57) ABSTRACT

A photoacoustic detector includes a sensing region for receiving atmospheric samples of a gas. A permeable membrane overlays a gas input port of the sensing region. The membrane is mechanically clamped to the sensing region by a compression force.

12 Claims, 4 Drawing Sheets

PHOTOACOUSTIC SENSOR DIFFUSION MEMBRANE ATTACHMENT STRUCTURE

FIELD

This application pertains to photoacoustic detectors. More particularly, the application pertains to such detectors which include a mechanical clamping structure to attach a gas permeable membrane to a sensing chamber.

BACKGROUND

Various types of photoacoustic sensors are known to detect gases. These include, Fritz et al., US Patent Application No. 2009/0320561, published Dec. 31, 2009 and entitled "Photoacoustic Cell"; Fritz et al., US Patent Application No. 2010/0027012, published Feb. 4, 2010 and entitled, "Photoacoustic Spectroscopy System"; Fritz et al., US Patent Application No. 2010/0045998, published Feb. 25, 2010 and entitled "Photoacoustic Sensor"; and Tobias, US Patent Application No. 2010/0147051, published Jun. 17, 2010 and entitled, "Apparatus and Method for Using the Speed of Sound in Photoacoustic Gas Sensor Measurements. The above noted published applications have been assigned to the assignee hereof, and are incorporated herein by reference.

Some known types of photoacoustic sensors incorporate resonant sensors. Others include gas valves. Members of another class of photoacoustic sensors incorporate diffusion membranes.

Diffusion membranes in photoacoustic sensors provide controlled ambient gas permeation into a sensing region. They also contribute to photoacoustic pressure confinement and bound a working volume of the photoacoustic chamber or sensing region.

In known sensors or detectors, this membrane is is attached with a layer of adhesive material. The adhesive material exhibits inherent problems which can impact functional performance of the membrane thus produce a strong impact on the functional performance of the photoacoustic sensor. These problems include: strong susceptibility to delaminate due to ambient conditions (temperature, humidity), and susceptibility to delaminate due to dimensional changes of a substrate as a function of ambient temperature variations (expansion and contraction). Membrane degradation, as described above, results in photoacoustic pressure variance or loss of the photoacoustic signal. Proper functioning of the diffusion membrane for these types of photoacoustic sensors is important for successful construction and functioning of the photoacoustic sensor.

DETAILED DESCRIPTION

Figure 1A:
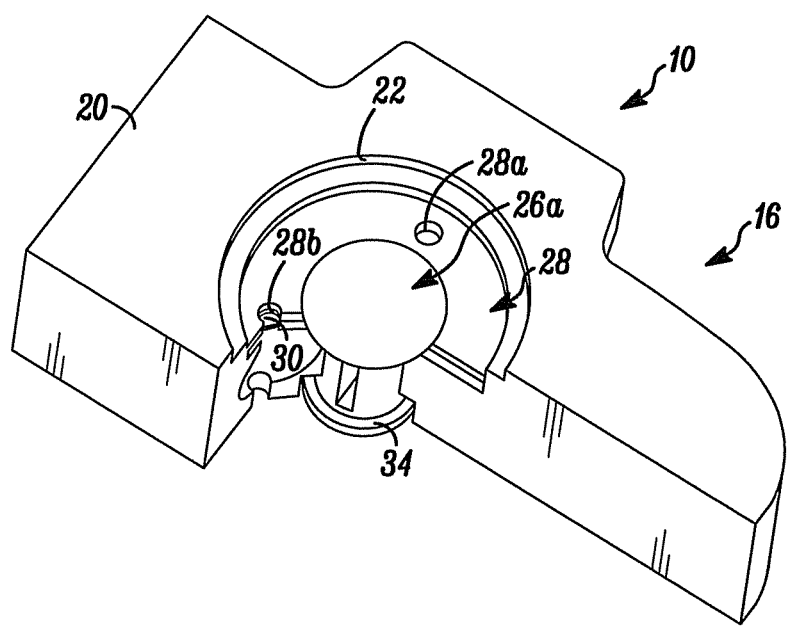
FIGS. 1A, 1B are over-all diagrams, partly broke away of a detector in accordance herewith.
Figure 1B:
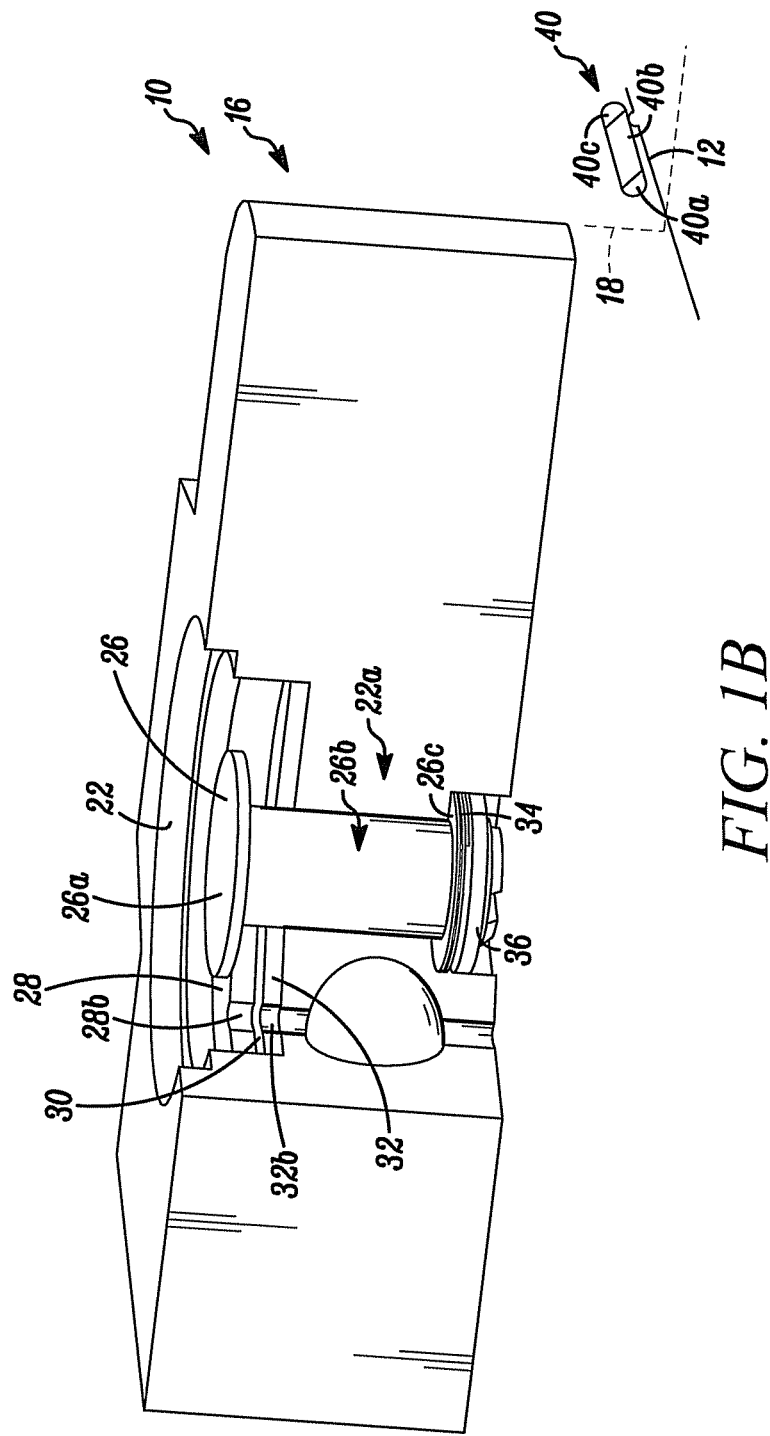
Figure 2:
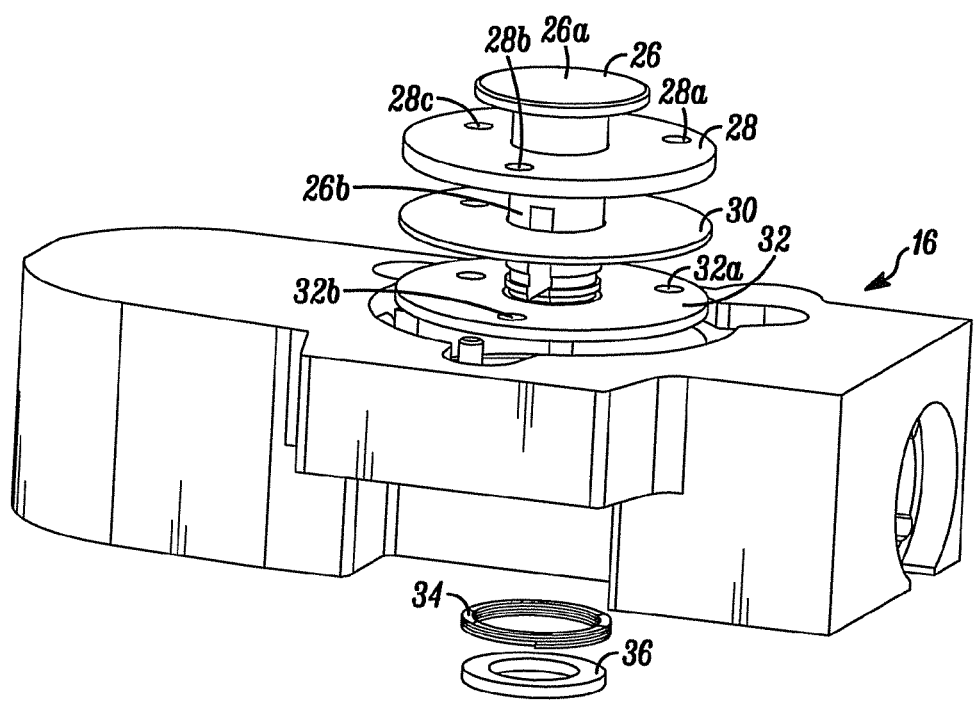
FIG. 2 is an exploded view of the detector of FIG. 1A, 1B.
Figure 3:
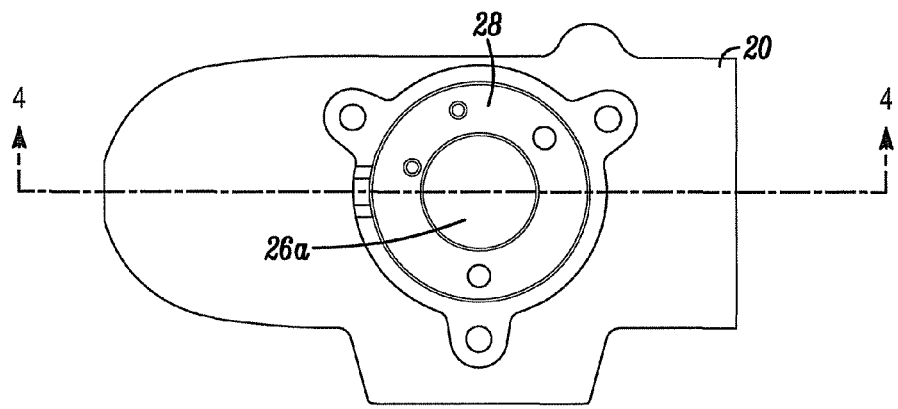
FIG. 3 is a top plan view of the detector of FIG. 2.
Figure 4:
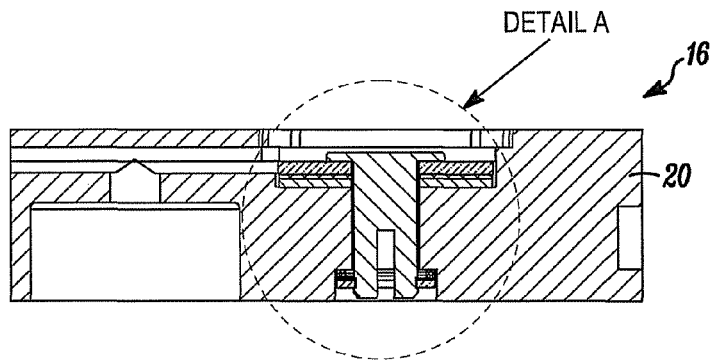
FIG. 4 is a sectional view of the detector of FIG. 3 taken along plane 4-4.

While embodiments can take many different forms, specific embodiments thereof are shown in the drawings and will be described herein in detail with the understanding that the present disclosure is to be considered as an exemplification of the principles hereof, as well as the best mode of practicing same. No limitation to the specific embodiment illustrated is intended.

Embodiments disclosed herein utilize a controlled mechanical force which ensures consistent pressure and retention of a diffusion membrane with respect to the photoacoustic chamber. A mechanical feature provides a capability of self-adjustment of a pressure value due to dimensional variation of the photoacoustic chamber. Unlike the prior art, the disclosed embodiment advantageously does not rely on or use any form of adhesive material. Instead, a compression force, which could be annular, is applied to the membrane.

The implementation is accomplished by utilization of wave spring material with the compression properties selected for application. As an alternative to the wave spring, other metallic or plastic spring arrangements or elastomers can be utilized. The chosen spring component applies uniform pressure distribution to the membrane through the use of a shaft, pressure plate and retaining ring.

FIGS. 1-5 illustrate various details of an embodiment of the present disclosure. A photoacoustic detector 10 includes a housing 12 which carries an upper structure 16 which is coupled to a sensing chamber or cell 18. Structure 16 defines a recess 22 and carries therein a gas permeable membrane which is held in place by a mechanical clamp 22a which applies a compression force.

The clamp 22a has an enlarged head 26a which is attached to an elongated shaft 26b. The head 26a abuts a pressure plate 28 which applies an annular compression force on the membrane 30 which overlays a gasket 32. If desired, the compression force could be applied to only portions of the membrane 30.

Figure 5:
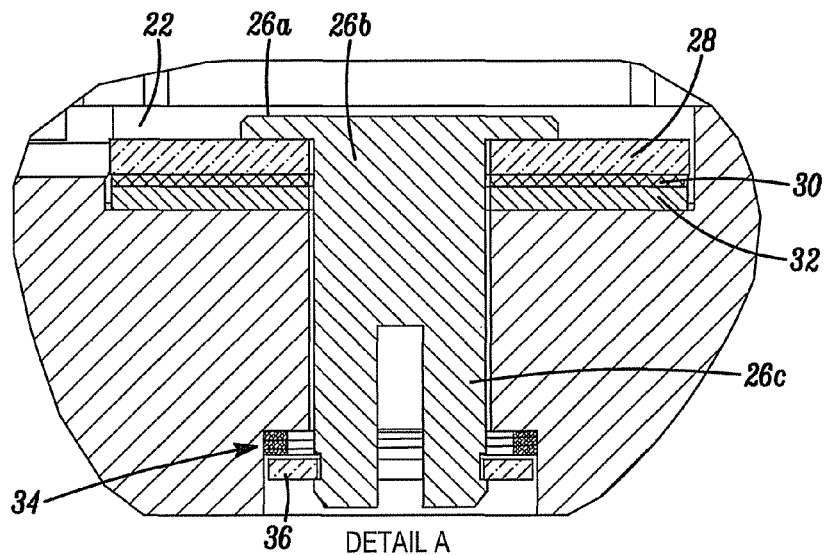
FIG. 5 is an enlarged view of Detail A of FIG. 4.

Clamp 22a is held in place in element 16 by a spring element 34 and a retaining ring 36 carried at a free end 26c of the shaft 26b. Plate 28 is compressed against the membrane 30 by the head 26a and the retaining ring 36 which locks to shaft 26b with a snap fit, as best shown in FIG. 5. Openings 28a, b in plate 28 and 32a, b in gasket 32 provide a path to/from the membrane 30 through which gas can permeate into the sensing chamber 18.

Detector 10 can also include control circuits 40 carried by housing 12. Control circuits 40 can be implemented with a programmable processor 40b which executes pre-stored control programs 40a. A radiant energy source 40c can also be coupled to the processor 40b.

From the foregoing, it will be observed that numerous variations and modifications may be effected without departing from the spirit and scope hereof. It is to be understood that no limitation with respect to the specific apparatus illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

The invention claimed is:

1. A photoacoustic detector comprising:
    a sensing chamber having an ambient gas input port;
    a gas permeable membrane which closes the ambient gas input port; and
    a mechanical clamping structure which attaches the gas permeable membrane to the sensing chamber;
    wherein the mechanical clamping structure includes a first element that clamps the membrane to a portion of the chamber, and a second element which is connected to the first element and to the chamber;

wherein the first element comprises an annular plate;

wherein the second element comprises a shaft with an enlarged head where the head abuts the plate.

2. A detector as in claim 1 where the first and second elements form clamp.

3. A detector as in claim 1 where the clamping structure includes a spring biased retainer.

4. A detector as in claim 3 where the retainer is carried at an end of the second element displaced from the first element.

5. A detector as in claim 4 where the retainer engages a portion of the sensing chamber.

6. A detector as in claim 1 where the first element includes an annular gasket where the head, the membrane and gasket form a multi-layer, substantially planar assembly with the membrane sandwiched between the plate and the gasket.

7. A detector as in claim 6 which includes a spring biased retainer.

8. A detector as in claim 7 where the retainer is carried on one end of the second element, displaced from the enlarged head.

9. A detector as in claim 6 which includes a housing which carries the sensing chamber and clamping structure along with control circuits.

10. A detector as in claim 9 which includes a source of radiant energy and a microphone all of which are carried by the housing and coupled to the control circuits.

11. A detector as in claim 10 where the control circuits determine the presence of an alarm condition.

12. A detector as in claim 10 where the control circuits include a programmed processor, and, pre-stored executable instructions.

\* \* \* \* \*